United States Patent [19]  [11] 4,129,648
Collier et al.  [45] Dec. 12, 1978

[54] METHOD FOR REDUCING ENDOGENOUS PROSTAGLANDIN SYNTHESIS

[76] Inventors: Harry O. J. Collier, 23 Campden Hill Rd., London, W.8.; Sheikh A. Saeed, 14 Eastcote Ave., South Harrow, Middlesex; Cyril Schneider, 71 Redway Dr., Whitton, Twickenham, all of England; Frank Mannuzza, 855 Oakside La., Park Forest South, Ill. 60466

[21] Appl. No.: 853,305

[22] Filed: Nov. 21, 1977

[51] Int. Cl.² .............. A61K 35/14; A61K 35/16; A61K/37/02
[52] U.S. Cl. ................................. 424/101; 424/177
[58] Field of Search ..................... 424/101, 424/177

[56] References Cited
U.S. PATENT DOCUMENTS
3,920,625 11/1975 Andersson et al. ............ 424/101

Primary Examiner—Sam Rosen
Attorney, Agent, or Firm—James D. McNeil

[57] ABSTRACT

A high molecular weight extract of mammalian blood plasma and serum proteins of the group Cohn fraction IV, Cohn subfraction $IV_1$, $IV_4$ and haptoglobin, have been found to contain activity which inhibits endogenous prostaglandin synthetase. This extract is therefore of utility in treating or alleviating pathological conditions associated with excessive or unbalanced snythesis of endogenous prostaglandins, for example, in reducing bronchoconstriction or treating arthritis. For this purpose, the extract may be administered by injection, by inhalation, or topically.

22 Claims, 1 Drawing Figure

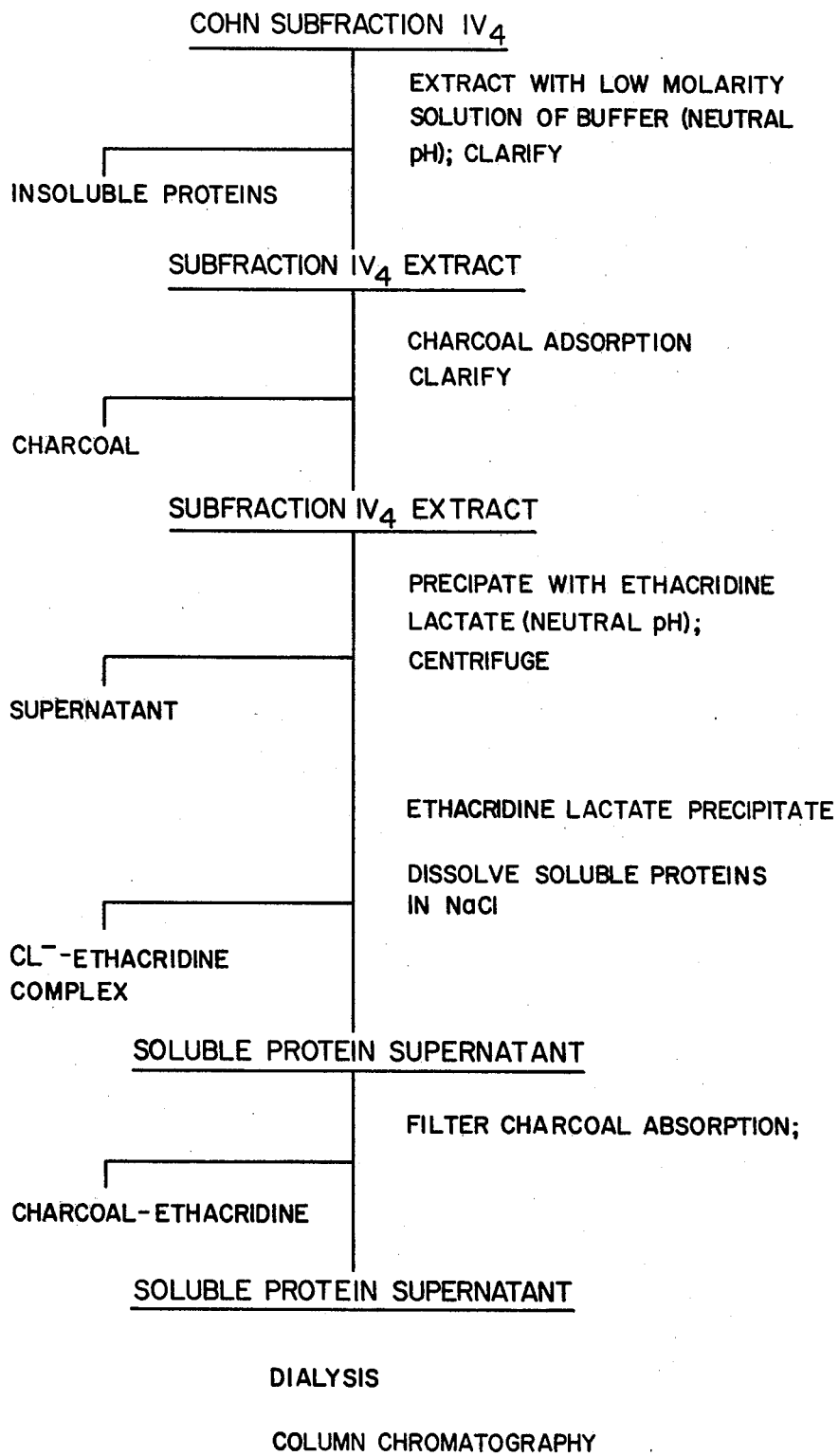

METHOD FOR REDUCING ENDOGENOUS PROSTAGLANDIN SYNTHESIS

BACKGROUND OF THE INVENTION

This invention relates to the inhibition of endogenous prostaglandin synthesis, and provides a method for treating or alleviating pathological conditions associated with excessive or unbalanced synthesis of endogenous prostaglandins (PG). In particular, the invention relates to the therapeutic treatment of the bronchoconstriction of asthma and of the inflammation of rheumatoid arthritis.

Although prostaglandins are a natural ingredient of body tissues and fluids, they can elicit or intensify a variety of untowards effects, including vomiting, diarrhoea, cough, inflammation and pain. Research has indicated, for example, that PGs produce inflammation and pain and also potentiate the inflammatory effects of other mediators. [See *Nature New Biol.*, 236, 141–142 and 240, 200–203 (1972) and *Nature*, 246, 217–219, (1973)].

$PGE_2$, (and to a lesser extent, $PGF_{2\alpha}$), has been demonstrated to be present in exudates from inflamed tissues and has been shown to be produced by untoward stimulation. [See *J. Pharm. Pharmac.* 21, 216–128 (1969); *Pharm. Res. Commun.* 3, 13–19 (1971); and Prostaglandin Synthetase Inhibitors, 121–133 Raven, New York (1974)]. Since, under normal conditions, the tissue concentration of PGs is low, the release of PG at sites of inflammation is theorized to be due to biosynthesis of the PGs.

Excessive or unbalanced synthesis of prostaglandins can therefore be harmful. It occurs, for example, in rheumatoid arthritis and other forms of inflammation and inflammatory pain, in asthma, in endotoxin shock, and in certain pathological conditions, such as the diarrhoea frequently associated with the presence of carcinoid tumors.

Prostaglandins are synthesized from unsaturated C-20 fatty acids, e.g., arachidonic acid, by an enzyme complex, prostaglandin synthetase, in the presence of a suitable cofactor. [See *Biochim. Biophys. Acta*, 90, 204 and 207 (1964)]. Sheep and bovine seminal vesicles (BSV) have been found to possess high activity for synthesizing prostaglandins from arachidonic acid; because of their greater availability, the majority of biosynthetic studies involving conversion of arachidonic acid into prostaglandins have been conducted using BSV.

Because PG synthesis occurs by the PG synthetase-catalyzed oxidative cyclization of arachidonic acid, measurement of inhibition of this synthesis can be accomplished by reacting a substance to be tested for inhibitory properties with arachidonic acid in the presence of PG synthetase. The amount of PG synthesized from the arachidonic acid in the presence of the test substance can be measured against the amount of PG synthesized in the absence of the test substance.

We have found that certain extracts or fractions of mammalian blood plasma have the property of inhibiting the in vitro synthesis of prostaglandins. These extracts can, therefore, be used to reduce or inhibit the activity of endogenous prostaglandin synthetase syand thereby treat or alleviate pathological conditions of the kinds already mentioned. The extracts which inhibit synthesis of prostaglandins are Cohn fraction IV, Cohn subfraction $IV_1$, Cohn subfraction $IV_4$ and the haptoglobins.

DESCRIPTION OF THE PRIOR ART

The prior art most relevant to the present invention, known by the applicants, is described below. In *J. Pharm. Pharmac.*, 24, 669 (1972), the authors disclose the isolation of a substance from human serum which reportedly demonstrated activity in the carrageenin oedema test in rats, i.e., anti-inflammatory activity.

The substance is described as being "peptide-like" and having a low molecular weight, in contradistinction to the high molecular weightserum extract of the present invention. The authors describe a procedure whereby pooled human serum is mixed with trichloroacetic acid and the precipitated proteins removed by centrifugation. The supernatant is then subjected to fractionation on a column of Sephadex G25 fine and four fractions separated. The third fraction was found to contain tryptophan plus the "active substance". The tryptophan was removed, and the supernatant remaining was tested for activity. For convenience, the authors described the tryptophan-free supernatant as fraction IV; this is not the Cohn fraction IV referred to in the present invention, since it is clear that the high molecular weight protein fraction would be present in the material precipitated by addition of the trichloroacetic acid. Since the authors assign a relatively low molecular weight of 12,000 to the "active" material, the net teaching of the authors is away from ascribing anti-inflammatory properties to the high molecular weight serum extract of the present invention.

A second relevant literature reference is *Nature*, 254, 444–446 (1975). The authors reported that a fraction isolated from normal human plasma by a method described in *J. Pharm. Pharmac.*, 25, 881–886 (1973) contained an anti-inflammatory substance.

The 1973 article describes the isolation of an anti-flammatory substance which is a small molecule. The authors disclose that the results suggest a compound with a molecular weight of 1000 or less. The 1975 article describes isolation of an anti-inflammatory "active" substance having a low molecular weight of 500 or less, from normal human plasma. In addition, the authors describe the anti-inflammatory mode of action as involving circulating leukocytes as a major factor, eg., Arthus reactions and the accumulation of polymorphonuclear and mononuclear cells into pleural and other inflammatory exudates. The authors specifically state that the anti-inflammatory activity of their low molecular weight fraction does "not involve an interference with either the release or action of chemical mediators of inflammation such as histamine, 5-hydroxytryptamine, kinins or prostaglandins."

British Pat. No. 1,426,039 discloses an aqueous solution of human serum haptoglobin and claims a process for its preparation. The patentee discloses that it is known that the presence of excess amount of free hemoglobin in the blood is usually accompanied by renal disorders which are often fatal. The patentee proposes administration of a haptoglobin preparation to a patient suffering from an excess of hemoglobin. There is no disclosure of the inhibition of endogenous prostaglandin synthesis.

Thus, none of the prior art articles, or the patent discussed above, disclose or suggest that a high molecular weight extract of human blood plasma and serum, obtained as disclosed and claimed in the present invention, is effective in inhibiting endogenous prostaglandin synthesis by reducing or inhibiting the activity of prostaglandin synthetase.

SUMMARY OF THE INVENTION

The present invention is directed to a method of reducing or inhibiting endogenous PG synthesis. The invention includes: a therapeutic method of reducing or inhibiting endogenous prostaglandin synthesis in an individual for whom such therapy is indicated, comprising administering to the individual an amount of a high molecular weight mammalian blood plasma or serum extract effective to reduce or inhibit the activity of prostaglandin synthetase, selected from the group consisting of Cohn fraction IV, Cohn subfraction $IV_1$, Cohn subfraction $IV_4$ and haptoglobin; a therapeutic method of reducing the inflammation associated with rheumatoid arthritis; and a therapeutic method of reducing the bronchoconstriction associated with asthma.

DETAILED DESCRIPTION OF THE INVENTION

The high molecular weight mammalian blood plasma or serum extract of the present invention was tested for PG synthesis-inhibiting properties by determining the ability of the extract to inhibit the conversion of arachidonic acid into $PGE_2$ and $PGF_{2\alpha}$ by PG synthetase present in BSV, in the presence of optimal amounts of the cofactor glutathione, (reduced form). Specifically, the inhibitory properties of the extract were determined by a cascade bioassay technique [Collier et al., Brit. J. Pharmac., 58, 193-199 (1976)] involving measurement of prostaglandin activity against response.

We have found that samples of mammalian serum extract obtained in the manner described below powerfully inhibit the ability of the prostaglandin synthetase of bovine seminal vesicles to convert arachidonic acid into $PGE_2$ and $PGF_{2\alpha}$ in the presence of optimal amounts of the cofactor glutathione (reduced form).

As explained in detail hereinbefore, the inhibiting activity is associated with the α-globulin fraction (Cohn fraction IV) of mammalian plasma. Of the different subfractions of Cohn fraction IV, subfraction $IV_1$ and $IV_4$ were most active; subfraction $IV_4$, purified as described to yield haptoglobin, is most preferred.

While we have theorized that the therapeutic effectiveness of the plasma extracts, in reducing the inflammation of arthritis induced by administration of Freunds adjuvant and in reducing bronchoconstriction, is attributable to inhibition of excess or unbalanced endogenous prostaglandin synthesis, we do not wish to be bound to any such theory.

The inhibitory activity is progressively reversed by the addition of increasing amounts of hemoglobin. This observation strongly suggests that the high molecular weight extract is similar in composition to the known blood protein haptoglobin.

Haptoglobin is the name given to a small group of circulating blood glycoproteins characterized by a high affinity for hemoglobin. Haptoglobins are glycoproteins having a molecular weight of 85,000 to 400,000. One major function of haptoglobin appears to be its ability to form a complex with any hemoglobin liberated from the red blood corpuscles by intra-vascular hemolysis. The complex so-formed is removed from the blood stream by the reticuloendothelial system. Various methods have been proposed for the determination of haptoglobin, mainly based on its ability to bind stoichiometrically with hemoglobin.

In addition to the experimental observation with hemoglobin, other reasons for associating the serum extract used in this invention with haptoglobin are: the addition of hemoglobin to the serum extracts capable of inhibiting the prostaglandin synthetase of BSV progressively reverses its inhibitory effect; polycrylamide gel electrophoresis of the purified active fraction in the presence of hemoglobin produces bands of peroxidase activity which are characteristic of the hemoglobin-haptoglobin complex; and, it is known that haptoglobin is concentrated in Cohn subfraction $IV_4$, which, as described later, drastically inhibits prostaglandin synthesis.

As indicated hereinafter, the property of inhibiting prostaglandin synthesis has been found in samples tested of extracts of mammalian serum and plasma. The activity has been found in extracts of serum of plasma of the dog, guinea pig, horse, cow, rabbit, rat and human. The extracts of mammalian serum which exhibit the highest activity are Cohn IV fractions. The activity is increased by further fractionation into $IV_1$ and $IV_4$ subfractions. Cohn subfraction $IV_4$ of, for example, human and cow sera, is commercially available and can be therapeutically used to inhibit prostaglandin synthesis. Cohn subfraction $IV_1$ and $IV_4$ can be generally obtained by fractionating blood samples at about $-5°$ C. with successive portions of 8 percent, 25 percent, 18 percent and 40 percent ethyl alcohol. [See J. Am. Chem. Soc., Vol. 68, pp. 495-575 (1946)].

In particular it has been found that Cohn subfraction $IV_4$ can be purified to remove substances such as albumin, to yield a purified subfraction $IV_4$ which is predominantly haptoglobin and which can be therapeutically administered. Following is a procedure which we have used to obtain haptoglobin.

This procedure could be used on any mammalian plasma or serum. The procedure was based on ammonium sulphate fractionation of the aqueous extract of human plasma Cohn subfraction $IV_4$ followed by ion exchange chromatography. For example, the extract can be chromatographed on diethylaminoethylcellulose. All manipulations were performed at 0° to 4° C. and centrifugations were conducted at 600g for 30 minutes unless otherwise specified. The solid ammonium sulphate was finely pulverized before use.

STEP 1 Ammonium sulphate fractionation

To 1 litre of a solution in distilled water containing 10 mg/ml of human plasma Cohn subfraction $IV_4$, solid ammonium sulphate was added in small portions with stirring until the solution was 35 percent saturated. The precipitate was removed by centrifugation and solid ammonium sulphate was then slowly added to the supernatant until the solution was 50 percent saturated. Stirring was continued throughout the addition and for 1 hour after the last addition of the salt. After standing for 2 hours at 4° C. with occasional agitation, the suspension was centrifuged for 60 minutes. The clear yellow supernatant solution was discarded, and the precipitate was dissolved in a small volume of water and dialyzed for 24 hours against frequent changes of distilled water, and then concentrated by lyophilization. The powder so obtained was dissolved in 0.01 M sodium acetate buffer at a pH of about 5, and centrifuged to remove any insoluble material. The clear supernatant was then used in the next step.

STEP 2 Chromatography on diethylaminoethyl cellulose

A jacketed chromatographic column (2.7 × 70 cm) was packed with diethylaminoethyl cellulose equilibrated with 0.01 M sodium acetate buffer at pH 5. Twenty ml of the solution obtained in step 1 containing approximately 1 g of protein were used for the chromatographic fractionation. The temperature of the column was maintained at 4° C. by circulation of cold water. A gradient former was used to produce acetate buffer having a linear gradient from 0.01 to 0.5 M. The proteins were eluted from the column at a rate of 1 ml per minute. The fraction collector was operated on a time basis and set to collect fractions of 15 ml each. The protein concentration in each fraction was determined by measuring absorption at 280 nm. The fractions were then assayed for activity against prostaglandin synthetase. The eluate fractions containing such activity were combined and concentrated using a polyethylene glycol. The haptoblogin obtained from Cohn subfraction IV$_4$ was then dialyzed for 72 hours against several changes of distilled water and lyophilized.

The procedure described utilizes standard purification techniques wherein the precipitant is added at a given concentration, the precipitate formed is discarded and a greater concentration of the precipitant is added to the supernatant form the dissolved material to further precipitate the desired substance. Alternately, the purification can be carried out in one step, depending upon the purity desired. The amount of saturation by addition of ammonium sulphate is not critical. For example, the ammonium sulphate can be added until the solution is from about 30 to 35 percent saturated. The supernatant can be from about 45 to 55 percent saturated in the second step.

CASCADE ASSAY SYSTEM

The ability of the purified mammalian serum extract to inhibit the enzymatic conversion of arachidonic acid by prostaglandin synthetase obtained from BSV was determined by bioassay on tissues which are known to be contracted by naturally occurring PGs. Segments of rat or hamster stomach fundus (stomach strip) were obtained as described in *Brit. J. Pharmacol.* Vol. 5, 173 (1950), Vol. 6, 32 (1953), Vol. 12, 344 (1957), and Vol. 23, 351 (1964). The superfusion technique introduced by Gaddum [*Brit J. Pharmacol.* 6, 321 (1953)] involves tying one end of the stomach strip preparation to the bottom of a tissue chamber and the other end to a force displacement transducer for continuous tension recording. The tension is adjusted to between 1.5 and 2.0 grams. The tissue preparations are left undisturbed with no solution for at least 15 minutes prior to testing. The tissue chamber has an external water jacket to enable temperature control of the tissues. Water at 40° C. is circulated in the water jacket.

The technique consists of dropwise bathing the tissue with a nutrient solution of Kreb's-Ringer bicarbonate bubbled with a mixture of 95 percent $O_2$ and 5 percent $CO_2$ warmed to 37° C. Antagonists are added to the Kreb's solution to eliminate the possibility of smooth muscle responses being due to stimulation of cholinergic, adrenergic, serotonin or histamine receptors. The fluid is circulated by means of a roller pump and is allowed to drip over the tissues at a flow rate of from about 5 to 10 ml/minute.

A dose of standard $PGE_2$ is put over the tissues by means of the roller pump and the tissue response measured by recording the tissue contraction. A volume of the test solution is then given to the tissue. If the response to the test solution is less than the response to the standard solution, a lower volume of standard is added, to give a lower response than the test response. By this method, the test is always bracketed between two standards, one with a higher response and one with a lower response. To calculate the test value, a logarithmic graph is plotted of the standard value in ng of $PGE_2$/ml solution, against the tension response (in mm). The test value obtained is expressed in ng. $PGE_2$ per volume of test solution injected. Alternately, the protein content of the solution can be determined by known techniques, such as the biuret reaction or Kjeldahl method, and the test value expressed in ng. $PGE_2$ per mg of protein of the test solution. In the dose range used (5–20 ng), $PGE_2$ contracted the fundus tissue.

This technique allows a greater biological sensitivity for biological assays in comparison with tests which involve tissue immersion, since the test solutions are not highly diluted. An additional advantage is that a compound can be tested simultaneously in several tissues by vertical tissue arrangement.

The following solutions were prepared for use in the cascade assay technique.

A. Kreb's-Ringer Solution

The following compounds were added to 5 liters of distilled water:

| | |
|---|---|
| NaCl | 34.5 gm |
| KCl | 1.75 gm |
| $CaCl_2$ | 1.9 gm |
| $KH_2PO_4$ | 0.8 gm |
| $MgSO_4$ | 1.45 gm |
| $NaHCO_3$ | 10.5 gm |
| Glucose | 5.0 gm |

B. Combined Antagonists Solution

The following compounds were made up to 40 ml saline, 0.9 percent (w/v), solution:

| | |
|---|---|
| Hyoscine | 5 mg |
| Mepyramine | 5 mg |
| Phenoxybenzamine | 5 mg |
| Propanolol | 150 mg |
| Methysergide | 10 mg |

C. Standard Solutions (1) $PGE_2$

Dissolve 1 mg $PGE_2$ in 1 ml of ethanol (96 percent v/v) = 1 mg/ml

Dilute for working standard 10 µg/ml, 100 ng/ml in 0.9 percent (w/v) saline.

The test solution was prepared by mixing together in a standard assay tube a solution of 50 mM phosphate buffer, 0.25 mM EDTA $Na_2$, 1.3 mM reduced glutathione (GSH), 0.5 ml of 15 mg/ml BSV powder solution dissolved in a phosphate buffer, at a pH of 7.4, ionic strength of 50 mM, and an appropriate volume of the purified serum extract or isotonic saline as control.

Enzymatic reaction was initiated by the addition of 61 µM sodium arachidonate. The assay tube was aerated at 37° C. with gentle shaking. After 15 minutes had elapsed, the reaction was stopped by adding 2.0 ml of 0.2 M citric acid. The mixture was then extracted with a 16 ml portion of ethylacetate. After centrifugation for 5 minutes at 600g, 10 ml of the ethylacetate layer was removed and evaporated to dryness in vacuo.

The residue obtained was dissolved in a 400 μl portion of ethanol (96 percent v/v). A 100 μl aliquot of this solution was diluted 50-fold with Kreb's-Ringer solution for cascade assay tests.

The force displacement transducer, tissue chamber and accompanying apparatus were set up as described previously. The roller pump was adjusted to pump the 95 percent $O_2$ - 5 percent $CO_2$ Kreb's-Ringer bicarbonate nutrient solution over the tissues at a flow rate of from 5 to 8 ml/minute.

The stomach strip was adjusted to allow the Kreb's-Ringer solution to drip onto the top of the strip, down the strip and off the bottom into the funnel.

During testing, the tissues were set up as described and allowed to stabilize with no reagent present for at least 15 minutes. A 20 ng dose of standard $PGE_2$ was then given by injecting the standard into the funnel and allowing the Kreb's-Ringer solution to wash the standard solution down over the stomach strip.

All experiments included blank controls in which arachidonic acid and the other reagents were incubated with PG synthetase which had been boiled for 3 minutes to inactivate PG synthetase, and extracted as above. The controls containing boiled enzyme were used to provide a baseline against which production in the tubes containing unboiled (active) enzyme could be measured in the presence and absence of test materials. The difference between test and control tubes indicated the amount of prostaglandin produced during the period of experimental incubation.

As shown in Table 1, this property of inhibiting PG synthesis has been found in various mammalian serum and plasma. Chicken serum did not inhibit PG synthesis.

As shown in Table 2, unfractionated mammalian sera at concentrations of 25 percent volume for volume or less, inhibited prostaglandin production by 70 percent or more.

Tests on different fractions of human plasma protein have shown that the inhibitory activity is associated with the α-globulin fraction (Cohn fraction IV), and that Cohn fractions, I, II, III, V and VI have little or no activity. Specifically, Cohn fractions I, II, III, V and VI were inactive at concentrations of 1.5 mg/ml and less, but fraction IV was active at concentrations of 50, 500 or 1500 micrograms per milliliter. Of the different subfractions of Cohn fraction IV, that designated $IV_4$, is the most effective. Table 2 compares the efficacy of Cohn fraction IV, $IV_1$ and $IV_4$ prepared as well known in the art by Cohn's low temperature alcohol fractionation technique referred to earlier.

TABLE 1

| Inhibition by various sera of prostaglandin synthesis | | | | | |
|---|---|---|---|---|---|
| Serum concentration | Mean percent inhibition of PG Production ± s.e.* | | | | |
| per cent v/v | Human | Dog | Rat | Rabbit | Mare | Chicken |
| 0.05 | 13.7 ± 5.8 | NT | NT | NT | NT | NT |
| 0.5 | 34.7 ± 13.7 | 14.0 ± 4.5 | 29.7 ± 4.91 | 2.1 ± 1.2 | 15.0 ± 9 | NA |
| 2.5 | NT | NT | 65.6 ± 8.56 | NT | NT | NT |
| 5.0 | 88.7 ± 2.2 | 61.0 ± 2.1 | 93.3 ± 2.14 | 16.8 ± 9 | 25.0 ± 3 | NA |
| 25.0 | 90.0 ± | 97.7 ± | NT | 91.5 ± | 91.0 ± | NA |

TABLE 1-continued

| Inhibition by various sera of prostaglandin synthesis | | | | | |
|---|---|---|---|---|---|
| Serum concentration | Mean percent inhibition of PG Production ± s.e.* | | | | |
| per cent v/v | Human | Dog | Rat | Rabbit | Mare | Chicken |
| | 3.5 | 0.38 | | 0.9 | 1 | |

NT — Not Tested
NA — Not Active
s.e. — Plus or minus the standard error of the mean

TABLE 2

| Inhibitory activity of human plasma Cohn fractions IV, $IV_1$ and $IV_4$ against PG synthesis | | | |
|---|---|---|---|
| Concentration ($\mu g\ ml^{-1}$) | Mean percentage inhibition of PG production ± s.e. | | |
| | IV | $IV_1$ | $IV_4$ |
| 50 | 13.4 ± 4.6 | 7.8 ± 7.5 | 25.0 ± 13.0 |
| 500 | 23.8 ± 2.6 | 10.5 ± 5.8 | 53.0 ± 7.7 |
| 1500 | 73.0 ± 3.2 | 39.4 ± 0.96 | 73.0 ± 1.8 |

It is now generally recognized that PG's play a major role in the inflammatory process and in the generation of inflammatory pain. In 1971, aspirin-like drugs were shown to inhibit PG release from human platelets, to inhibit PG release from perfused dog spleen and to inhibit PG synthesis in guinea pig lung. Inhibition of PG release by aspirin, salicyclic acid, indomethacin, and other aspirin-like drugs and has been demonstrated by researchers and correlated with anti-inflammatory activity.

It is also recognized that asthma is a disease condition wherein excess PG is present in lung tissue. Administration of arachidonic acid or arachidonate induces bronchoconstriction accompanied by the presence of increased amounts of PG. This bronchoconstriction can be measured by increase of airway resistance and lung compliance.

The ability of Cohn subfraction $IV_4$, and Cohn $IV_4$ purified as described earlier to yield haptoglobin, to prevent the in vitro synthesis of prostaglandins has been demonstrated by measuring its ability to antagonize the effects of sodium arachidonate in the guinea pig in increasing airway resistance and decreasing lung compliance. The ability of Cohn subfraction $IV_4$ and haptoglobin to reduce the transient hypertension caused by administration of sodium arachidonate in the guinea pig was also measured. These tests were carried out as follows.

MEASUREMENTS OF DYNAMIC COMPLIANCE AND RESISTANCE IN THE ANAESTHETIZED GUINEA PIG

Male albino guinea pigs weighing 400–600 g each (Dunkin Hartley strain) were anesthetized by administration of sodium pentobarbitone, 60 mg/kg intraperitoneally. The trachea was cannulated for artificial ventilation by a Starling pump (5–8 ml at 72 strokes per minute) via a Fleisch 0000 pneumatachograph. The difference in pressure across this device was measured with a Grass differential pressure transducer. This gives a flow signal which was fed into a Hewlett-Packard 8816A analogue computer. Transpulmonary pressure (TPP) was measured with another differential pressure transducer via side arms to the thoracic cavity and the tracheal cannula. The signals for low and TPP were applied to the analogue computer so that there was approximately 180° phase difference. The computer derived the dynamic compliance and resistance from the in-going signals. Drugs were administered intravenously via the external jugular vein. A 1 mg/ml solution of sodium arachidonate was prepared as follows. Arachidonic acid (10 mg, 99 percent pure) was dissolved in 0.2 ml absolute ethanol and the solution was diluted to 10 ml with 0.2 percent weight per volume sodium carbonate solution. Challenge doses of 100–500 micrograms per kg were given via the cannulated left external jugular vein and "washed in" with 0.5 ml of 0.85 percent weight per volume sodium chloride solution (saline) containing 10 units/ml of heparin. These doses were given at 30 minute intervals to produce a large but submaximal bronchoconstriction. After 2 or 3 similar responses to the same dose of sodium arachidonate had been obtained, the test substance in saline (0.1 to 1 ml) was injected intravenously. At various times thereafter, a challenge was given. The test substances used were as follows: human plasma Cohn subfraction IV$_4$ (unheated or heated to 60° C. for 15 minutes and cooled to 20° C.); Cohn subfraction IV$_4$ purified as described above; dexamethasone sodium phosphate; hydrocortisone sodium succinate; aldosterone; aspirin calcium salt; indomethacin sodium salt; and a drenocorticotrophin (ACTH).

MEASUREMENTS OF MEAN ARTERIAL BLOOD PRESSURE IN THE GUINEA PIG

The left carotid artery was cannulated for recording blood pressure with a Grass pressure transducer (Consolidated Dynamics 0.75 cm Hg type 4L221) linked to a Devices twin channel polygraph via a CD2D pre-amplifier. Electrocardiograms were recorded using a DC6 pre-amplifier linked to the Devices polygraph. The chart records displayed the analogue computer-derived dynamic compliance and airway resistance, transpulmonary pressure, tracheal flow, mean arterial blood pressure, and electrocardiogram.

The results obtained are shown in the following Tables:

TABLE 3

Inhibition by human plasma Cohn subfraction IV$_4$, haptoglobin obtained from IV$_4$ by ammonium sulphate procedure, and some anti-inflammatory drugs of the increased airway resistance and decreased lung compliance induced by sodium arachidonate in the guinea pig. All drugs were given intravenously.

| Treatment | Dose mg/kg | Time of challenge after treatment | Mean % Inhibition (± s.e.) of increased airway resistance | educed dynamic lung compliance | No. of Observations |
|---|---|---|---|---|---|
| Haptoglobin* | 5 | 45 sec | 31.8 ± 4.7 | 27.4 ± 5.3 | 5 |
| " | 20 | " | 44.3 ± 6.7 | 34.3 ± 7.4 | 3 |
| " | 50 | " | 67.7 ± 0.3 | 49.0 ± 3.2 | 3 |
| " | 100 | " | 67.0 ± 8.0 | 64.0 ± 0 | 2 |
| Haptoglobin* heated to 60° C 15 min | 5 | 45 sec | 10.3 ± 5.2 | 6.3 ± 6.3 | 3 |
| Cohn Subfraction IV$_4$ | 5 | 45 sec | 36.7 ± 1.2 | 35.3 ± 2.3 | 3 |
| " | 20 | " | 53.4 ± 5.3 | 49.5 ± 4.3 | 13 |
| " | 60 | " | 60.0 ± 12 | 50.0 ± 0 | 2 |
| " | 60 | 10 min | 61.0 | 38.0 | 1 |
| " | 60 | 30 min | 56.0 | 32.0 | 1 |
| " | 60 | 45 min | 53.0 | 0 | 1 |
| " | 100 | 45 sec | 67.7 ± 4.2 | 67.3 ± 6.4 | 3 |
| Cohn Subfraction IV$_4$ heated to 60° C 15 min | 20 | 45 sec | 22.3 ± 4.6 | 24.3 ± 4.3 | 3 |
| Aspirin | 2 | 45 sec | 85.5 ± 3.5 | 71.5 ± 6.5 | 2 |
| " | 2 | 30 min | 91.0 ± 9.0 | 81.5 ± 7.5 | 2 |
| Indomethacin | 0.03 | 45 sec | 47.0 ± 15.8 | 58.7 ± 15.7 | 4 |
| " | 0.10 | " | 90.5 ± 9.5 | 85.5 ± 14.5 | 2 |
| ACTH | 25μ/kg | 30 min | 31.5 ± 24.5 | 16.5 ± 16.5 | 2 |
| " | " | 60 min | 55.5 ± 3.5 | 35.5 ± 2.5 | 2 |
| " | " | 90 min | 72.5 ± 12.5 | 62.5 ± 12.5 | 2 |
| 41 | " | 120 min | 68.5 ± 16.5 | 53.0 ± 3.0 | 2 |
| " | " | 150 min | 85.0 | 63.0 | 1 |
| " | 50μ/kg | 30 min | 52.0 | 67.0 | 1 |
| " | " | 60 min | 73.0 | 50.0 | 1 |
| " | " | 90 min | 73.0 | 67.0 | 1 |
| " | " | 120 min. | 91.0 | 75.0 | 1 |
| " | " | 150 min | 68.0 | 58.0 | 1 |
| " | " | 180 min | 59.0 | 75.0 | 1 |
| " | " | 210 min | 66.0 | 75.0 | 1 |
| " | " | 240 min | 67.0 | 75.0 | 1 |
| Dexamethasone | 3.85 | 10 min | 45.3 ± 12.2 | 35.0 ± 7.6 | 3 |
| " | " | 30 min | 65.0 ± 7.0 | 55.0 ± 5.0 | 2 |
| " | " | 60 min | 50.0 | 57.0 | 1 |
| " | " | 90 min | 33.0 | 54.0 | |
| " | " | 120 min | 25.0 | 43.0 | |
| " | " | 150 min | 17.0 | 34.0 | |
| " | " | 180 min | 8.0 | 37.0 | |
| Hydrocortisone | 15 | 45 sec | 24.0 ± 1.5 | 15.0 ± 7.5 | 1 |
| " | " | 10 min | 24.3 ± 6.8 | 21.3 ± 4.2 | 3 |
| " | " | 30 min | 46.2 ± 5.7 | 49.0 ± 9.7 | 4 |
| " | " | 60 min | 61.0 ± 3.0 | 44.0 ± 6.0 | 5 |
| " | " | 90 min | 54.0 | 25.0 | 2 |
| " | " | 120 min | 17.0 | 12.0 | 1 |
| Aldosterone | 0.04 | 30 min | 9.0 | 0 | 1 |
| " | 0.20 | " | 14.0 | 1.0 | 1 |
| " | 0.50 | " | 0 | 10.5 ± 6.5 | 2 |
| " | " | 60 min | 6.5 ± 6.5 | 5.0 ± 5.0 | 2 |

*obtained frm Cohn subfraction IV$_4$ by ammonium slphate purification

TABLE 4

Inhibition by human plasma Cohn subfraction $IV_4$, haptoglobin obtained from $IV_4$ by ammonium sulphate procedure and some anti-inflammatory drugs of transient hypertension induced by sodium arachidonate in the anaesthetized guinea-pig. All substances were given intravenously.

| Treatment | Dose mg/kg | Time of challenge after treatment | Mean % Inhibition (± s.e.) of hypertension | No. of Observations |
|---|---|---|---|---|
| Haptoglobin* | 5 | 45 sec | 34.5 ± 13.9 | 4 |
| " | 20 | " | 83.5 ± 16.5 | 2 |
| " | 50 | " | 90.0 ± 10.0 | 2 |
| " | 100 | " | 73.0 | 1 |
| Haptoglobin* heated to 60° C | 5 | 45 sec | 7.0 ± 7.0 | 2 |
| Cohn Subfraction $IV_4$ | 5 | 45 sec | 26.8 ± 1.8 | 2 |
| " | 20 | " | 57.0 ± 3.0 | 2 |
| " | 100 | " | 90.0 ± 10.0 | 2 |
| Cohn Subfraction $IV_4$ heated to 60° C | 20 | 45 sec | 32.0 | 1 |
| Indomethacin | 0.03 | 45 sec | 65.0 ± 2.1 | 2 |
| ACTH | 25μ/kg | 30 min | 24.0 ± 10.0 | 2 |
| " | " | 60 min | 28.5 ± 14.5 | 2 |
| " | " | 90 min | 49.0 ± 15.0 | 2 |
| " | " | 120 min | 53.5 ± 3.5 | 2 |
| " | " | 150 min | 17.0 | 1 |
| " | 50μ/kg | 30 min | 83.0 | 1 |
| " | " | 60 min | 67.0 | 1 |
| " | " | 90 min | 100.0 | 1 |
| " | " | 120 min | 67.0 | 1 |
| " | " | 150 min | 100.0 | 1 |
| " | " | 180 min | 83.0 | 1 |
| " | " | 210 min | 100.0 | 1 |
| " | " | 240 min | 100.0 | 1 |
| Hydrocortisone | 15 | 45 sec | 35.0 ± 2.0 | 2 |
| " | " | 10 min | 48.0 ± 18.0 | 2 |
| " | " | 30 min | 25.0 ± 25.0 | 2 |
| " | " | 60 min | 25.0 | 1 |

*Obtained from Cohn subfraction $IV_4$ by ammonium sulphate purification

The results reported in Table 3 show that all the substances tested, with the exception of aldosterone (a mineralocorticoid known not to possess anti-inflammatory activity) and the partially heat-inactivated test substances, markedly inhibited arachidonate-induced bronchoconstriction as determined by effects on airway resistance and dynamic lung compliance. Table 4 shows that the transient hypertension induced by intravenous injections of sodium arachidonate was similarly inhibited. Aspirin, indomethacin, ACTH, dexamethasone and hydrocortisone are well known anti-inflammatory agents in animals and man. Inhibition of bronchoconstriction induced by arachidonate in the guinea pig appears to be well correlated with known clinical anti-inflammatory activity. We have, therefore, concluded that human plasma Cohn fraction IV, subfraction $IV_1$, subfraction $IV_4$ and in particular, haptoglobin obtained from $IV_4$ by ammonium sulfate precipitation, possess potential anti-inflammatory activity in man in those disease conditions where prostaglandins or their inflammatory precursors are involved. These conditions include rheumatoid arthritis and asthma.

In other experiments, we have found that Cohn subfraction $IV_4$ lessens the intensity of arthritis induced by administration of Freunds adjuvant in the rat using the method of Newbould [Brit. J. Pharmacol., 21, 127–136 (1963)].

A suspension of 25 micrograms of killed ground Mycobacterium butyricum (DIFCO) in 50 μl of light liquid paraffin was injected into the plantar surface of the left hind foot of each of three groups of 12 rats on day 0. On days −1 to +3 and days 5–11, saline or Cohn subfraction $IV_4$, 2 mg/kg or 10 mg/kg, was injected subcutaneously. Foot swelling was measured daily using a micrometer placed sagitally. Analysis of the results on day 12 showed that, in comparison with saline, subfraction $IV_4$ both at 2 and 10 mg/kg subcutaneously given 1 day before and then daily (except day 4) until day 11, significantly ($p < 0.05$) reduced the swelling of the adjuvant-treated left hind foot and of the untreated right hind foot. The higher dose (10 mg/kg) also significantly (p $< 0.05$) reduced the incidence of swelling of the fore feet and totally suppressed the incidence of nodule in the tail ($p < 0.05$).

Studies of the ability of Cohn subfraction $IV_4$ to inhibit prostaglandin synthetase have shown that its activity in this respect is due to a proteinaceous constituent of the fraction. Thus, the activity cannot be extracted with a solvent for fats. The active ingredient is thermolabile and not dialyzable. The activity is not due to the presence of ceruloplasmin, transferrin, cholinesterase, glutathione, peroxidase, albumin or a lipoprotein.

Haptoglobin was obtained from Cohn subfraction $IV_4$ by a second procedure, illustrated in the drawing and described below. This second method was undertaken in an attempt to further characterize the proteinaceous constituent of the Cohn subfraction $IV_4$.

Cohn subfraction $IV_4$ was first extracted with a low molarity solution of a low ionic strength buffer; pH of about 7.0. The insoluble proteins precipitated were removed by centrifugation and filtration. A suitable buffer is tris (hydroxymethyl) aminoethane hydrochloride. The molarity can range from about 0.01 to 0.1 M, preferably about 0.06 M.

The Cohn subfraction $IV_4$ extract was subjected to charcoal adsorption to remove lipoproteins. About 1/2 g charcoal/gm of protein in extract was found to be suitable. The extract was clarified by filtration. Optionally the extract can be centrifuged prior to filtration. At this stage, the extract contained about 4–5 percent by weight protein. The extract was then treated with aqueous ethacridine lactate (monohydrate); $C_{18}H_{21}N_3O_4$ at a pH of about 7. The ethacridine is available under various trade designations, eg., Rivanol, Vucine Rimaon and Aerolactine. The ethacridine can range from about 0.16 to 0.4 percent; about 0.24 percent is preferred. The pH can range from about 7.0 to 8.5. $\beta$ globulins present in the Cohn subfraction $IV_4$ extract remain soluble in the supernatant. A pH of greater than 8.5 is undesirable, because at about 8.5, transferrin begins to co-precipitate out of solution along with the desired precipitate. Below about 7.0, increasing amounts of the desired proteinaceous material are left in solution.

The ethacridine precipitate was treated with 1M NaCl (5 percent) to dissolve soluble proteins. An insoluble $Cl^-$ ethacridine complex formed, leaving the soluble proteins in the supernatant. The supernatant was then adsorbed with charcoal to remove any minor remaining amounts of ethacridine and filtered.

The supernatant was then reconcentrated to about 5 percent protein content by ultrafiltration, and subjected to chromatographic procedures.

Various chromatographic techniques well known to those skilled in the art have been found satisfactory. These techniques include the steps of:

(1) fractionation on DEAE A50 ion-exchange resin (to separate residual $\beta$ globulin from $\alpha$ globulins. Based on protein similarity, the inter $\alpha, \alpha_1$ and $\alpha_2$ fractions are pooled).

(2) Cibacron affinity chromatography (to remove albumin), using Cibracron F-3GA blue dye, available from Ciba AG, Basel, Switzerland, attached to Sephadex G-75, available from Pharmacia, Uppsala, Sweden [See J. Chromatogr, 69: 209-214 (1972)]; and (3) gel permeation chromatography, involving the use of sephadex G100 (100,000 molecular weight exclusion); G150 (200,000 molecular weight exclusion); and sepharose 6B ($2.5 \times 10^6$ molecular weight exclusion).

The preferred embodiment involves, in the following order, as described above, step 2, and step 1, followed by step 3.

Optionally, the contaminating proteins (including albumin, one of the major contaminants) can be partially precipitated with ethacridine lactate at a pH of about 5, prior to the ethacridine precipitation at pH of about 7. However, it is preferable that the albumin be removed quantitatively by the cibacron/sepharose affinity chromatography procedure referred to above.

The sepharose 6B gel permeation chromatography procedure, in conjunction with the G100 and G150 column fractionations indicates that the Cohn human subfraction $IV_4$ subjected to the described treatment, has a molecular weight within the range of the molecular weight ascribed to haptoglobin, i.e., 80,000 to about 400,000. The data established the probability, based on distribution of the molecular weight exclusion, that the Cohn subfraction $IV_4$ has a lower molecular weight of slightly less than 100,000 with the most representative portion within the range 160,000 to 330,000. The molecular weight is described in terms of probability, since the results obtained by the chromatography procedures used are dependent upon the shape and size of the molecule being subjected to chromatographic procedure. Further, polyacrylamide gel electrophoresis indicates the presence of monomers and higher polymer forms, eg., dimers.

Experimental tests indicated that the haptoglobin obtained from Cohn subfraction $IV_4$ by the above procedure also demonstrated an ability to inhibit the prostaglandin synthetase of BSV, indicating that the haptoglobin obtained from Cohn $IV_4$ is of utility in treating or alleviating pathological conditions associated with excessive or unbalanced synthesis of endogenous PGs.

The term "individual" as utilized in this specification means a human being or an experimental animal that is a model for a human being. Medical indications for the use of the fraction of the present invention are any conditions in which it is desired to inhibit or restrict the production of prostaglandins within the individual, by restricting or inhibiting the biosynthesis of prostaglandin. The term "effective inhibitory effect" or any equivalent of that term means a significant reduction or restriction of prostaglandin synthesis.

The invention accordingly provides a method for treating or alleviating pathological conditions associated with excessive or unbalanced synthesis of endogenous prostaglandins which comprises administering to an individual having such a condition an amount of purified serum extract obtained as disclosed hereinabove, effective to reduce or control the said prostaglandin sythesis. While Cohn subfraction $IV_4$ can be used, it is preferred to obtain haptoglobin from $IV_4$ in the manner already described for therapeutic use.

Experimental studies have indicated that the effective fraction of blood protein has a half life in vivo in the blood of 5 to 7 days. As already explained, it has substantial affinity for hemoglobin, and is inactivated by combination with hemoglobin liberated from lysed red blood corpuscles. Very frequent doses of the prostaglandin synthetase inhibitor are not, therefore, required, and it is generally satisfactory to administer one or two doses each day.

While the purified serum extract which can be Cohn fraction IV, subfraction $IV_1$, $IV_4$ and haptoglobin from any mammal is effective in inhibiting prostaglandin synthetase, in order to avoid allergic reactions, it is desirable to use, in the treatment of humans, a purified blood plasma or serum extract derived from human blood, for example outdated blood from a blood bank. However, for veterinary purposes, a protein fraction from, for example, bovine plasma can be used.

It is generally preferred to administer the extract parenterally as a sterile aqueous solution. Such solutions may contain 20 to 100 mg/ml of extract and preferably about 50 mg/ml. The solution should be buffered to a pH of about 7.2 and may be rendered isotonic by incorporation of an appropriate solute. The injection may be, for example, intramuscular, subcutaneous or, in the case of treatment of arthritis, intra-articular. The solution might also be administered by intraveous infusion. The dosage may be, for example, from 50 to 500 milligram twice daily in the case of an adult weighing 70 kg. Since the extract is a normal constituent of blood, its toxicity is very low and it is therefore possible to exceed the recommended dose by a wide margin without adverse effect. Doses up to 10 to 15 grams can be administered daily to an adult without ill-effect.

Alternatively, the extract may be administered rectally, e.g. by suppository, sub-lingually, or by insufflation. The last of these methods is particularly appropriate for the treatment of asthma and other affections of the respiratory tract. For this purpose, the extract may be made up as a salt-free powder having a particule size below 5 microns, and therefore capable of being inhaled. Alternatively, a solution of the extract may be made into an aerosol by conventional techniques and the aerosol then inhaled. It is also possible to administer the extract in the form of nasal drops.

For the treatment of skin conditions associated with excessive or unbalanced synthesis of prostaglandins, the extract may be applied topically. Such conditions include eczema, acne, contact dermatitis and sunburn. For use in this way, the extract may be made up in a standard ointment or cream base compatible therewith in a concentration of, for example, 0.1 to 10 percent by weight. Such a composition may be applied to the affected area as required, for example, twice daily.

The effect of the extract in inhibiting synthesis of prostaglandins is likely to be enhanced by anti-inflammatory corticosteroids such as dexamethasone. It may, therefore, in some cases be advantageous to administer the extract in combination with such a corticosteroid. The latter may be used in a dosage known to be appropriate in the treatment of the pathological condition in question.

What is claimed is:

1. A therapeutic method of reducing or inhibiting endogenous prostaglandin synthesis in an individual for whom such therapy is indicated, comprising administering to the individual an amount of a high molecular weight mammalian blood plasma or serum extract effective to reduce or inhibit the activity of prostaglandin synthetase, selected from the group consisting of Cohn fraction IV, Cohn subfraction $IV_1$, Cohn subfraction $IV_4$ and haptoglobin.

2. A method as claimed in claim 1 wherein the high molecular weight extract is haptoglobin.

3. A method as claimed in claim 2 wherein the haptoglobin is obtained from Cohn subfraction $IV_4$ by (a) adding ammonium sulphate to Cohn $IV_4$ subfraction and collecting the protein fractions precipitated, dissolving the protein fractions in water and chromatographing the aqueous protein fractions or by (b) extracting Cohn subfraction $IV_4$ with a low molarity solution of buffer at a pH of about 7.0 to form a precipitate of insoluble proteins and a supernatant, adsorbing the supernatant with charcoal to remove lipoproteins, adding ethacridine lactate to the supernatant at a pH of from about 7.0 to 8.5 to form a precipitate, dissolving the precipitate in NaCl to form a protein-containing supernatant, and chromatographing the aqueous protein supernatant.

4. A method as claimed in claim 3 wherein the ammonium sulphate is added to Cohn $IV_4$ subfraction until the subfraction is from about 30 to 35 percent saturated, to form a precipitate and a supernatant, discarding the precipitate and adding ammonium sulphate to the supernatant until the subfraction is from about 45 to 55 percent saturated.

5. A method as claimed in claim 3 wherein the subfraction is human Cohn $IV_4$.

6. A therapeutic method according to claim 1 wherein the high molecular weight serum extract is administered to reduce the inflammation associated with rheumatoid arthritis.

7. A therapeutic method according to claim 3 wherein the haptoglobin is administered to reduce the inflammation associated with rheumatoid arthritis.

8. A therapeutic method according to claim 1 wherein the high molecular weight serum extract is administered to reduce the bronchoconstriction associated with asthma.

9. A therapeutic method according to claim 3 wherein the haptoglobin is administered to reduce the bronchoconstriction associated with asthma.

10. A therapeutic method as claimed in claim 1 in which the amount of extract administered is from 50 to 500 mg twice daily for an adult.

11. A therapeutic method as claimed in claim 1 in which the extract is administered by injection.

12. A therapeutic method as claimed in claim 11 in which the extract is administered as a sterile aqueous isotonic solution buffered to a pH of about 7.2.

13. A therapeutic method as claimed in claim 1 in which the extract is administered rectally, sub-lingually or by insufflation.

14. A therapeutic method of reducing or inhibiting endogenous prostaglandin synthesis in an individual for whom such therapy is indicated, comprising administering to the individual an amount of haptoglobin effective to reduce or inhibit the activity of prostaglandin synthetase wherein the haptoglobin is obtained by:
  (a) adding ammonium sulphate to human plasma Cohn $IV_4$ subfraction until the solution is about 35 percent saturated to form a precipitate and supernatant, and removing the precipitate;
  (b) dissolving the precipitate in water and adding to the solution ammonium sulphate until the solution is about 50 percent saturated, to form a precipitate and a supernatant and removing the precipitate;
  (c) dissolving the precipitate in water, dialyzing the dissolved precipitate, lyophilizing to obtain a powder, and dissolving the lyophilized powder in buffered solution at a pH of about 5 and removing any precipitate formed from the supernatant; and
  (d) chromatographing the supernatant.

15. A therapeutic method according to claim 14 wherein the haptoglobin is administered to reduce the inflammation associated with rheumatoid arthritis.

16. A therapeutic method according to claim 14 wherein the haptoglobin is administered to reduce the bronchoconstriction associated with asthma.

17. A therapeutic method of reducing or inhibiting endogenous prostaglandin synthesis in an individual for whom such therapy is indicated, comprising: administering to the individual in an amount of haptoglobin effective to reduce or inhibit the activity of prostaglandin synthetase, wherein the haptoglobin is obtained from Cohn $IV_4$ subfraction by:
  (a) removing insoluble proteins from the Cohn $IV_4$ subfraction by extraction with a low molarity solution of buffer at a pH of about 7.0 to form a supernatant and a precipitate;
  (b) adsorbing the supernatant with charcoal to remove lipoproteins;
  (c) adding ethacridine lactate to the supernatant at a pH of from about 7.0 to 8.5 to form a precipitate;
  (d) dissolving the precipitate in NaCl to form a protein-containing supernatant; and
  (e) chromatographing the aqueous protein supernatant.

18. A therapeutic method according to claim 17 wherein the haptoglobin is administered to reduce the inflammation associated with rheumatoid arthritis.

19. A therapeutic method according to claim 17 wherein the haptoglobin is administered to reduce the bronchoconstriction associated with asthma.

20. A therapeutic method of reducing or inhibiting endogenous activity of prostaglandin synthetase in an individual for whom such therapy is indicated, comprising administering to the individual an effective amount of haptoglobin obtained from Cohn IV$_4$ subfraction by:
(a) removing insoluble proteins from Cohn IV$_4$ subfraction by extraction with low molarity solution of buffer at a pH of about 7.0 to form a supernatant and a precipitate;
(b) adsorbing the supernatant with charcoal to remove lipoproteins, and clarifying the supernatant;
(c) adding ethacridine lactate to the supernatant at a pH of about 7.0 to form a precipitate;
(d) dissolving the precipitate in NaCl to form a supernatant;
(e) reconcentrating the protein; and
(f) chromatographing the aqueous protein fraction.

21. A therapeutic method according to claim 20 wherein the haptoglobin is administered to reduce the inflammation associated with rheumatoid arthritis.

22. A therapeutic method according to claim 20 wherein the haptoglobin is administered to reduce the bronchoconstriction associated with asthma.

* * * * *